(12) United States Patent
Kim et al.

(10) Patent No.: US 11,383,864 B2
(45) Date of Patent: Jul. 12, 2022

(54) CAPSULE FILLING APPARATUS

(71) Applicant: CTC BIO, INC., Seoul (KR)

(72) Inventors: Seung Kyun Kim, Seoul (KR); Yun Jin Sung, Paju-si (KR); Bong-Sang Lee, Suwon-si (KR); Hong Ryeol Jeon, Suwon-si (KR)

(73) Assignee: CTO BIO, INC., Seoul (KR)

( * ) Notice: Subject to any disclaimer, the term of this patent is extended or adjusted under 35 U.S.C. 154(b) by 113 days.

(21) Appl. No.: 16/966,200

(22) PCT Filed: Oct. 18, 2018

(86) PCT No.: PCT/KR2018/012364
§ 371 (c)(1),
(2) Date: Jul. 30, 2020

(87) PCT Pub. No.: WO2019/151610
PCT Pub. Date: Aug. 8, 2019

(65) Prior Publication Data
US 2021/0039813 A1    Feb. 11, 2021

(30) Foreign Application Priority Data

Feb. 2, 2018 (KR) .................. 10-2018-0013559

(51) Int. Cl.
*B65B 5/10* (2006.01)
*A61J 3/07* (2006.01)
(Continued)

(52) U.S. Cl.
CPC .............. *B65B 5/103* (2013.01); *A61J 3/074* (2013.01); *A61K 9/4833* (2013.01); *B65B 35/12* (2013.01); *B65B 35/20* (2013.01); *B65B 2220/14* (2013.01)

(58) Field of Classification Search
CPC ......... B65B 5/103; B65B 35/12; B65B 35/20; B65B 2220/14; A61J 3/074; A61J 3/03; A61K 9/4833; A61K 9/4808; Y10S 53/90
See application file for complete search history.

(56) References Cited

U.S. PATENT DOCUMENTS 3,527,015 A * 9/1970 Van Hostetler ......... A61J 3/074
                                                   53/468
4,501,307 A * 2/1985 Moser ..................... A61J 3/074
                                                   141/12
(Continued)

FOREIGN PATENT DOCUMENTS

CN      101134001 A     3/2008
JP      2544052 B2      10/1996
(Continued)

OTHER PUBLICATIONS

International Search Report dated May 3, 2019 for International Patent Application No. PCT/KR2018/012364, 4 pages with English translation.

*Primary Examiner* — Robert F Long
*Assistant Examiner* — Eduardo R Ferrero
(74) *Attorney, Agent, or Firm* — MH2 Technology Law Group, LLP

(57) ABSTRACT

Disclosed is a capsule filling apparatus. The capsule filling apparatus includes a supplying member configured to supply a tablet; a moving member configured to move the tablet supplied from the supplying member in a preset direction; a catching member configured to catch the tablet moved by the moving member by suction and insert the caught tablet into a capsule; and a capsule accommodating member located below the catching member so that the capsule is accommodated therein.

8 Claims, 13 Drawing Sheets

(51) Int. Cl.
  *A61K 9/48* (2006.01)
  *B65B 35/12* (2006.01)
  *B65B 35/20* (2006.01)

(56) References Cited

U.S. PATENT DOCUMENTS

| | | | | |
|---|---|---|---|---|
| 5,101,612 A | * | 4/1992 | Yamamoto | A61J 3/074 53/499 |
| 5,329,749 A | | 7/1994 | Yamamoto et al. | |
| 5,966,910 A | * | 10/1999 | Ribani | A61J 3/074 221/173 |
| 6,269,615 B1 | * | 8/2001 | Amborn | B65B 5/103 53/235 |
| 6,318,051 B1 | * | 11/2001 | Preiss | B65B 5/103 53/237 |
| 6,327,835 B1 | * | 12/2001 | Trebbi | A61J 3/074 53/53 |
| 6,425,422 B1 | * | 7/2002 | Trebbi | A61J 3/074 141/67 |
| 6,810,930 B2 | * | 11/2004 | Schlipf | A61J 3/074 141/130 |
| 6,925,782 B2 | | 8/2005 | Aylward | |
| 7,225,597 B1 | * | 6/2007 | Knoth | B65B 5/103 53/244 |
| 8,015,777 B2 | | 9/2011 | Yagyu et al. | |
| 8,220,657 B2 | | 7/2012 | Cicognani | |
| 2002/0195459 A1 | * | 12/2002 | Greenwald | G07F 17/0092 221/289 |
| 2005/0217752 A1 | * | 10/2005 | Facchini | A61J 3/074 141/146 |
| 2006/0191953 A1 | * | 8/2006 | Hiddink | B65B 35/06 221/289 |
| 2007/0095716 A1 | * | 5/2007 | Monti | B65B 5/103 206/531 |
| 2007/0289660 A1 | * | 12/2007 | Aylward | B65B 35/08 141/18 |
| 2008/0216452 A1 | * | 9/2008 | Moodley | B65B 25/145 53/454 |
| 2008/0223001 A1 | | 9/2008 | Monti | |
| 2009/0044495 A1 | * | 2/2009 | Aylward | B65B 35/46 53/473 |
| 2009/0241482 A1 | * | 10/2009 | Yagyu | A61J 3/074 53/475 |
| 2010/0011715 A1 | * | 1/2010 | Freudelsperger | B65B 35/06 53/493 |
| 2013/0118638 A1 | * | 5/2013 | Hopkins | B65B 1/366 141/1 |
| 2015/0098992 A1 | * | 4/2015 | Kim | A61K 31/4422 424/452 |
| 2017/0015446 A1 | * | 1/2017 | Frabetti | A61J 3/074 |

FOREIGN PATENT DOCUMENTS

| | | |
|---|---|---|
| JP | 2001-294204 A | 10/2001 |
| KR | 20-0196147 Y1 | 9/2000 |
| KR | 10-1029905 B1 | 4/2011 |
| KR | 10-1057642 B1 | 8/2011 |
| KR | 10-2012-0124727 A | 11/2012 |
| KR | 10-1595908 B1 | 2/2016 |
| KR | 10-1624155 B1 | 5/2016 |

* cited by examiner (a)　　　　　　(b)

CAPSULE FILLING APPARATUS

CROSS-REFERENCE TO RELATED APPLICATIONS

The present application is a U.S. National Stage application of PCT/KR2018/012364 filed Oct. 18, 2018, which claims priority to Korean Patent Application No. 10-2018-0013559 filed on Feb. 2, 2018, in the Republic of Korea, the disclosures of which are incorporated herein by reference.

The present disclosure relates to a capsule filling apparatus, and more particularly, to a capsule filling apparatus capable of improving a filling rate of tablets when the tablets are filled in a capsule.

BACKGROUND ART

Typically, tablets may be classified into an immediate-release type and an extended-release type. Here, if a patient needs to take all of a plurality of tablets, it is easier to take all of the plurality of tablets in one capsule, rather than to take each tablet separately.

FIGS. 1(a) and 1(b) are diagrams showing that tablets are filled using a capsule in a conventional capsule filling method.

In the conventional case, tablets 1 are inserted into a capsule 5 in a free-falling manner That is, the tablets 1 are dropped into the capsule 5 from a capsule filling device (not shown) located above the capsule 5. Here, in general, the tablet 1 is formed in a cylindrical shape so that a height of a lateral side 2 of the tablet 1 is smaller than a diameter of a base side 3 of the tablet 1. In the conventional technique, a plurality of tablets 1 are dropped into the capsule 5 in a state where the plurality of tablets 1 are placed in the capsule filling device (not shown) such that the base sides 3 of the plurality of tablets 1 are in contact with each other, namely such that the plurality of tablets 1 are placed in a horizontal direction. According to the method, the tablet 1 is inclined during falling and is arranged inside the capsule 5 in the inclined state (see X in FIG. 1(a)), or in severe cases, the tablet 1 is positioned upright inside the capsule 5 (see Y in FIG. 1(b)). If the tablets 1 are inclined or erected inside the capsule 5 as in FIGS. 1(a) and 1(b), the tablets 1 are not neatly filled in the entire space of the capsule 5, so the inside space of the capsule 5 is wasted. Thus, the number of tablets 1 that can be filled inside the capsule 5 is reduced, and the filling rate is low when the tablets 1 is filled.

DISCLOSURE

Technical Problem

The present disclosure is designed to solve the problems of the related art, and therefore the present disclosure is directed to providing a capsule filling apparatus capable of improving a filling rate of tablets when the tablets are filled in a capsule, by preventing the tablets from being inclined or erected.

Also, the present disclosure is directed to providing a capsule filling apparatus, which may easily fill tablets where a height of a lateral side of the tables is smaller than a diameter of a base side thereof, in a capsule.

Technical Solution

In one aspect of the present disclosure, there is provided a capsule filling apparatus, comprising: a supplying member configured to supply a tablet; a moving member configured to move the tablet supplied from the supplying member in a preset direction; a catching member configured to catch the tablet moved by the moving member and insert the caught tablet into a capsule; and a capsule accommodating member located below the catching member so that the capsule is accommodated therein.

Also, the supplying member may be coupled to the catching member to move together with the catching member.

In addition, the supplying member may include a cover portion coupled to the catching member; and a tablet arranging portion formed inside the cover portion so that the tablet is arranged therein.

Also, the tablet may be formed in a cylindrical shape so that a height of a lateral side of the tablet is smaller than a diameter of a base side of the tablet, and a plurality of tablets may be arranged in the tablet arranging portion such that lateral sides of the plurality of tablets are in contact with each other.

In addition, the moving member may include a support on which the tablet supplied from the supplying member is placed; and a driving unit coupled to the support to move the support.

Also, the tablet may be formed in a cylindrical shape so that a height of a lateral side of the tablet is smaller than a diameter of a base side of the tablet, and the tablet may be placed on the support so that the lateral side of the tablet comes into contact with the support.

In addition, the capsule filling apparatus may further comprise an aligning member disposed between the catching member and the moving member such that the tablet collides with the aligning member to fall down while the moving member is moving, so that the base side of the tablet comes into contact with the support.

Also, the catching member may insert the tablet into the capsule by moving into the capsule in a state of catching the tablet by suction.

In addition, the catching member may catch the tablet located at the moving member when the moving member moves toward the capsule accommodating member, and the catching member may insert the tablet into the capsule accommodating member when the moving member moves away from the capsule accommodating member.

Also, the capsule accommodating member may be provided in plural, and the plurality of the capsule accommodating members may be provided such that any one capsule accommodating member among the plurality of capsule accommodating members is located below the catching member by rotation.

Advantageous Effects

According to embodiments of the present disclosure, since the catching member catches tablets by suction and fills in a capsule, it is possible to prevent the tablets from being inclined or erected when the tablets are filled in a capsule, thereby improving a filling rate of the tablets when the tablets are filled in the capsule.

Also, tablets where a height of a lateral side of the tables is smaller than a diameter of a base side thereof may also be easily filled in the capsule by means of the supplying member, the moving member and the catching member.

BEST MODE

Figure 1:
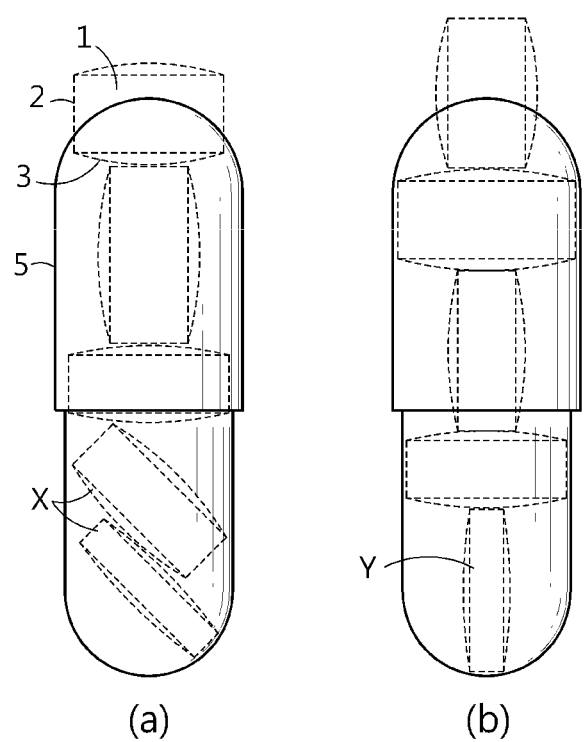
FIG. 1 is a diagram showing that tablets are filled using a capsule in a conventional capsule filling method.

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

In the drawings, the size of each element or a specific part of the element may be exaggerated, omitted, or schematically illustrated for convenience and clarity of a description. Thus, the size of each element does not entirely reflect the actual size of the element. A detailed description of well-known functions or elements associated with the present disclosure will be omitted if it unnecessarily obscures the subject matter of the present disclosure.

The term, 'combine' or 'connect' as used herein, may refer not only to a case where one member and another member are directly combined or directly connected but also a case where one member is indirectly combined with another member via a connecting member or is indirectly connected.

Figure 13:
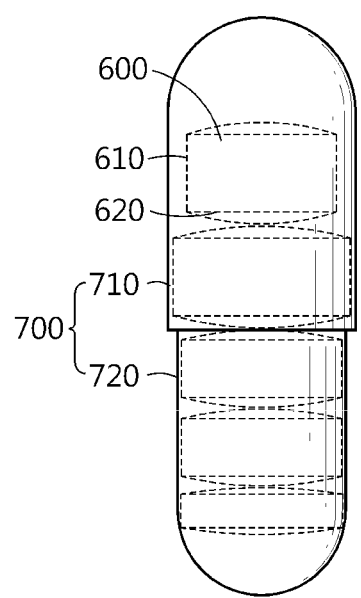
FIG. 13 is a diagram showing that tablets are filled using a capsule using the capsule filling apparatus according to an embodiment of the present disclosure.

The term 'horizontal direction' used in this means that a tablet 600 is arranged as shown in FIG. 13 such that a diameter of a base side 620 (see FIG. 13) of the tablet 600 is directed to the horizontal direction, and the term 'vertical direction' means that the tablet 600 is arranged such that the diameter of the base side 620 of the tablet 600 is directed to the vertical direction, for example in the same direction as the tablet 3 in FIG. 1(b) that is arranged upright (see Y in FIG. 1(b)). The thickness of the tablet 600 means a height of a lateral side 610 of the tablet 600 when the diameter of the base side 620 of the tablet 600 is arranged to face the horizontal direction.

Figure 2:
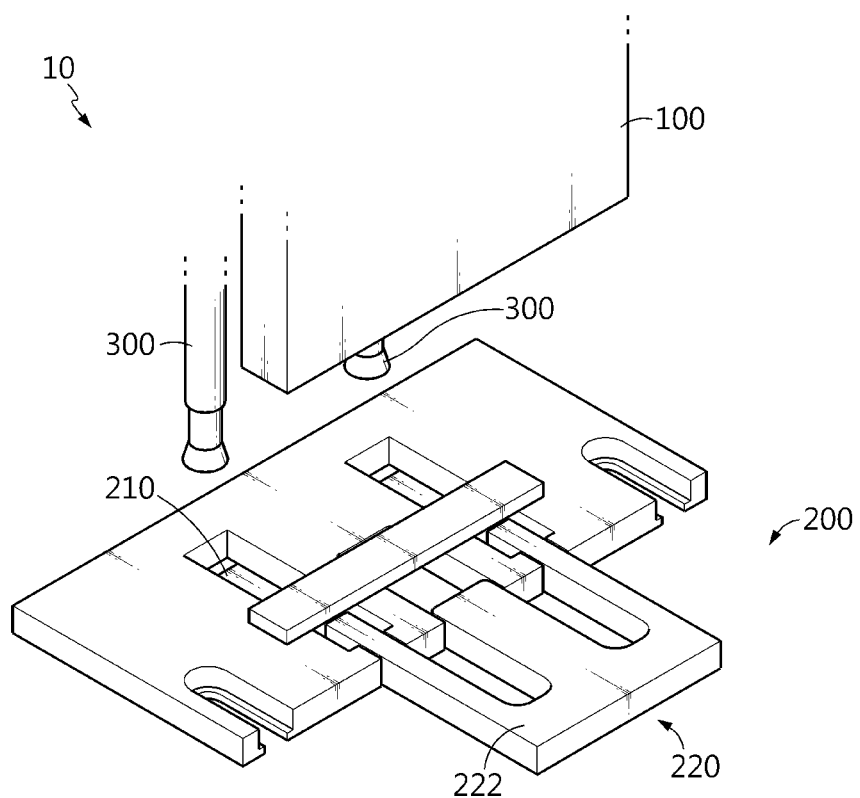
FIG. 2 is a schematic perspective view showing a capsule filling apparatus according to an embodiment of the present disclosure.

FIG. 2 is a schematic perspective view showing a capsule filling apparatus according to an embodiment of the present disclosure, FIGS. 3 to 12 are diagrams for illustrating a process of filling tablets in a capsule using the capsule filling apparatus according to an embodiment of the present disclosure, and FIG. 13 is a diagram showing that tablets are filled using a capsule using the capsule filling apparatus according to an embodiment of the present disclosure.

Referring to FIGS. 2 to 12, a capsule filling apparatus 10 according to an embodiment of the present disclosure includes a supplying member 100, a moving member 200, an catching member 300, and a capsule accommodating member 400.

The supplying member 100 supplies the tablets 600 to the moving member 200. The supplying member 100 may be provided as a hopper that accommodates the tablets 600. Referring to FIGS. 3 to 12, the tablets 600 may be provided to be accommodated in the supplying member 100 along the height direction from top to bottom.

The supplying member 100 may be provided to operate separately from the catching member 300, but may also be coupled to the catching member 300 to move together with the catching member 300. That is, when the catching member 300 catches the tablet 600 by suction and moves toward a capsule 700 to insert the tablet 600 into the capsule 700, the supplying member 100 may move toward the moving member 200 to supply a new tablet 600 to the moving member 200.

The supplying member 100 may include a cover portion 110 and a tablet arranging portion 120. The cover portion 110 is coupled to the catching member 300. The cover portion 110 may have various shapes, and may be provided as a length member so that the tablet 600 may be accommodated in the supplying member 100 along the height direction, and may be arranged in a height direction, namely in a vertical direction. The tablet arranging portion 120 is formed inside the cover portion 110, and the tablets 600 are arranged in the tablet arranging portion 120. In addition, the tablet 600 may be supplied to the moving member 200 while moving along the tablet arranging portion 120. Here, the tablet 600 is formed in a cylindrical shape so that the height of the lateral side 610 of the tablet 600 may be smaller than the diameter of the base side 620 of the tablet 600 (see FIG. 13). That is, the tablet 600 is provided such that a diameter of the tablet 600 is larger than the thickness thereof. Here, a plurality of tablets 600 are arranged inside the tablet arranging portion 120 so that the lateral sides 610 of the plurality of tablets 600 comes into contact with each other. That is, in the conventional technique, the tablets 600 fall in a state where the tablets are horizontally arranged, so the tablets are inclined during the fall. However, in the embodiment of the present disclosure, even though the tablet 600 have the same shape, referring to FIGS. 3 to 12, the tablets 600 are supplied from the supplying member 100 to the moving member 200 in a state of being vertically arranged, thereby preventing the tablets 600 from being inclined while being supplied.

A door (not shown) may be coupled to a lower side of the supplying member 100. That is, if the door (not shown) is opened, one of the plurality of tablets 600 arranged in the tablet arranging portion 120 is discharged and supplied to the moving member 200. In addition, if the door (not shown) is closed, the discharge of other tablets 600 is restricted.

The moving member 200 moves the tablet 600 supplied from the supplying member 100 in a preset direction. Referring to FIGS. 3 to 12, the supplying member 100 and the capsule accommodating member 400 are disposed on different straight lines in the vertical direction, and the catching member 300 and the capsule accommodating member 400 are disposed on the same straight line in the vertical direction. That is, the capsule accommodating member 400 is spaced from the supplying member 100 in the left direction based on FIG. 3. In addition, the moving member 200 moves the tablet 600 supplied from the supplying member 100 toward the capsule accommodating member 400. That is, the moving member 200 moves the tablet 600 by a spaced distance between the capsule accommodating member 400 and the supplying member 100 in the left and right direction. As described above, the spaced gap is formed between the capsule accommodating member 400 and the supplying member 100 in the left and right direction based on FIG. 3 such that the tablets 600 placed in the vertical direction on the moving member 200 is located in a horizontal direction while being moved toward the capsule accommodating member 400. This will be described later in detail.

Figure 5:
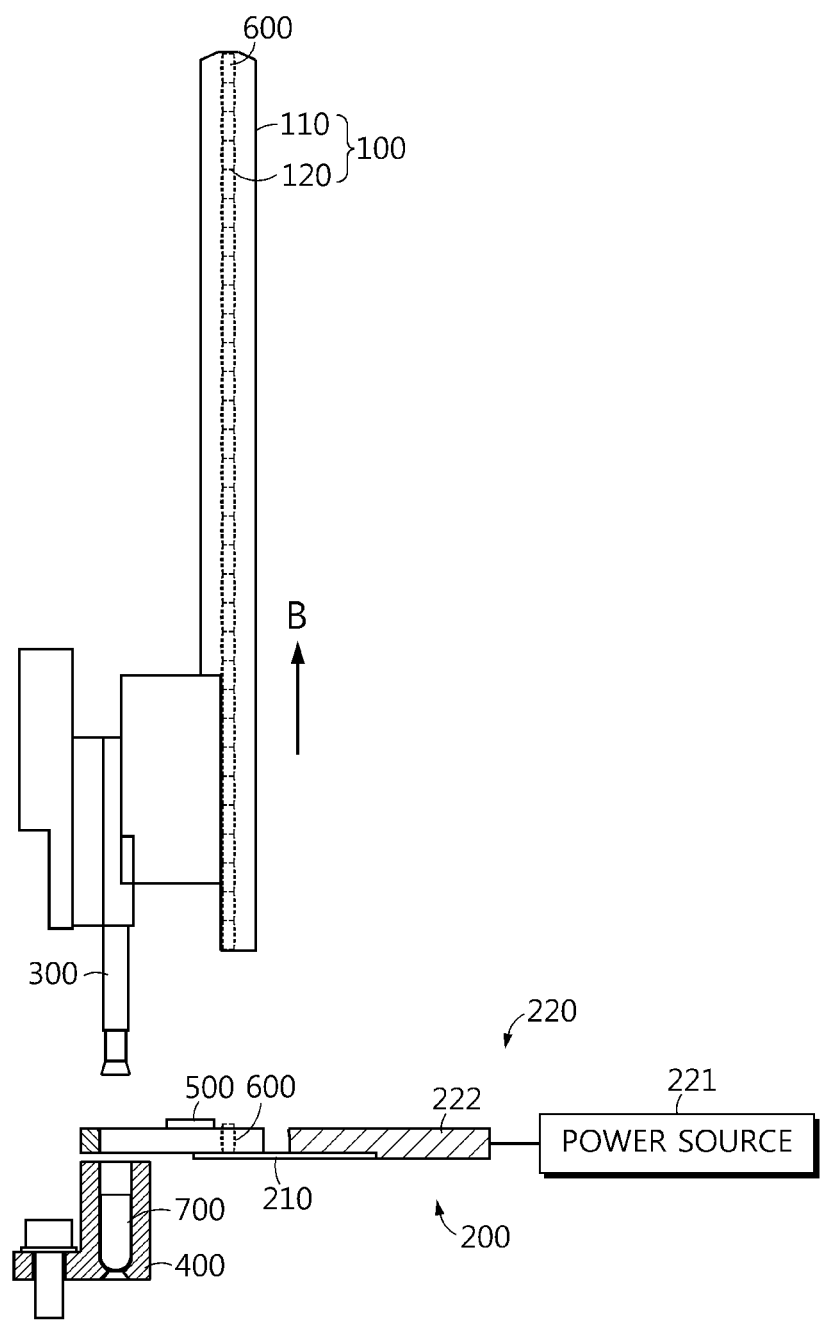

The moving member 200 may include a support 210 and a driving unit 220. The tablet 600 supplied from the supplying member 100 is placed on the support 210 (see FIG. 5). Here, the tablet 600 is formed in a cylindrical shape as described above so that the height of the lateral side 610 of the tablet 600 is smaller than the diameter of the base side 620 of the tablet 600, and the tablet 600 is placed such that the lateral side 610 of the tablet 600 is in contact with the support 210. That is, since the tablet 600 is supplied from the supplying member 100 to the moving member 200 in a state of being vertically arranged, the tablet 600 is placed on the support 210 in the vertical direction as shown in FIG. 5. Meanwhile, since the tablet 600 is inserted into the capsule 700 in the horizontal direction, that the tablet 600 placed in the vertical direction on the moving member 200 needs to fall down so as to be placed in the horizontal direction. For this, an aligning member 500 may be disposed between the catching member 300 and the moving member 200. That is, when the support 210 moves toward the catching member 300 by the driving unit 220, the tablet 600 placed in the vertical direction collides with the aligning member 500 and falls down to be aligned in the horizontal direction (see FIGS. 6 to 8). Accordingly, the base side 620 of the tablet 600 may come into contact with the support 210. The driving unit 220 may be coupled to the support 210 to move the support 210. The driving unit 220 may include various kinds of power sources 221 such as a motor, and may include a power transmission plate 222 coupled to the power source 221 such as a motor and the support 210, respectively. That is, the power from the power source 221 such as a motor may be transmitted to the support 210 through the power transmission plate 222.

The catching member 300 catches by suction the tablet 600 moved by the moving member 200 and inserts the tablet 600 into the capsule 700. Here, the catching member 300 may catch the tablet 600 in various ways, for example in an air suction type, without being limited thereto. The capsule accommodating member 400 accommodating the capsule 700 is disposed below the catching member 300. If the catching member 300 is not provided, the tablet 600 moving from the moving member 200 may freely fall into the capsule 700. In this case, the tablet 600 may be inclined or erected inside the capsule 700, which is a problem of the conventional technique. However, in the capsule filling apparatus 10 according to an embodiment of the present disclosure, the catching member 300 catches by suction the tablet 600 moved from the moving member 200, and the catching member 300 and the tablet 600 move downward together in a state where the catching member 300 catches the tablet 600 by suction, so that the catching member 300 and the tablet 600 enter the capsule 700 together. Thus, the adsorption of the catching member 300 is stopped in a state where the tablet 600 is correctly arranged, and then the catching member 300 moves upward. Accordingly, the tablet 600 may be filled inside the capsule 700 accurately in the horizontal direction without being inclined or erected inside the capsule 700 (see FIG. 13). In the conventional case of FIGS. 1(a) and 1(b), only 4 tablets 1 may be filled inside the capsule 5. However, referring to FIG. 13, in the embodiment of the present disclosure, 5 tablets 600 may be filled inside the capsule 700. Here, the catching member 300 may be configured to insert the tablet 600 into the capsule 700 by moving into the capsule 700 in a state of catching the tablet 600. That is, the catching member 300 catches the tablet 600 located at the moving member 200 when the moving member 200 moves toward the capsule accommodating member 400, and the catching member 300 inserts the tablet 600 into the capsule accommodating member 400 when the moving member 200 moves away from the capsule accommodating member 400.

The catching member 300 may be provided in plural in one line. For example, referring to FIG. 2, two catching members 300 may be provided in one line. However, the number of catching members 300 is not limited thereto, and various numbers of catching members 300 may be provided if necessary. In addition, the catching member 300 may be provided to a plurality of lines. That is, in a first line, a first tablet 600 may be filled in the capsule 700, and in a second line, a second tablet 600 may be filled in the capsule 700. The number of lines may vary depending on the number of tablets 600 filled in the capsule 700. Here, the first tablet 600 and the second tablet 600 may be the same type of tablet 600 or different types of tablets 600. In addition, a line in which powder, granules, or the like is filled in the capsule 700 in addition to the tablet 600 may be provided. Accordingly, one capsule 700 may be filled with powder or granules along with the tablet 600.

The capsule accommodating member 400 is located below the catching member 300 and the capsule 700 is accommodated therein. Here, the capsule 700 accommodated in the capsule accommodating member 400 may correspond to a part of the entire capsule 700. For example, referring to FIG. 13, the capsule 700 may be composed of an upper capsule portion 710 and a lower capsule portion 720, and the upper capsule portion 710 and the lower capsule portion 720 may be coupled to configure one complete capsule 700. In this case, the lower capsule portion 720 may be accommodated in the capsule accommodating member 400, and if the tablet 600 is completely filled in the lower capsule portion 720, the upper capsule portion 710 may be coupled to the lower capsule portion 720 to complete the capsule 700. However, in this specification, the capsule 700 accommodated in the capsule accommodating member 400 may refer to the lower capsule portion 720.

The capsule accommodating member 400 may be provided in plural. For example, any one capsule accommodating member 400 among the plurality of capsule accommodating members 400 may be positioned below the catching member 300 by rotating the plurality of capsule accommodating members 400. In addition, if the tablet 600 is completely filled in the capsule 700 inside the capsule accommodating member 400 located below the catching member 300, another capsule accommodating member 400 may be positioned below the catching member 300 by rotation. In this way, the tablet 600 may be filled successively in each of the capsules 700 accommodated in the plurality of capsule accommodating members 400, which allows automation of the filling process of the capsules 700.

Hereinafter, the operation and effects of the capsule filling apparatus 10 according to an embodiment of the present disclosure will be described with reference to the drawings.

Figure 3:
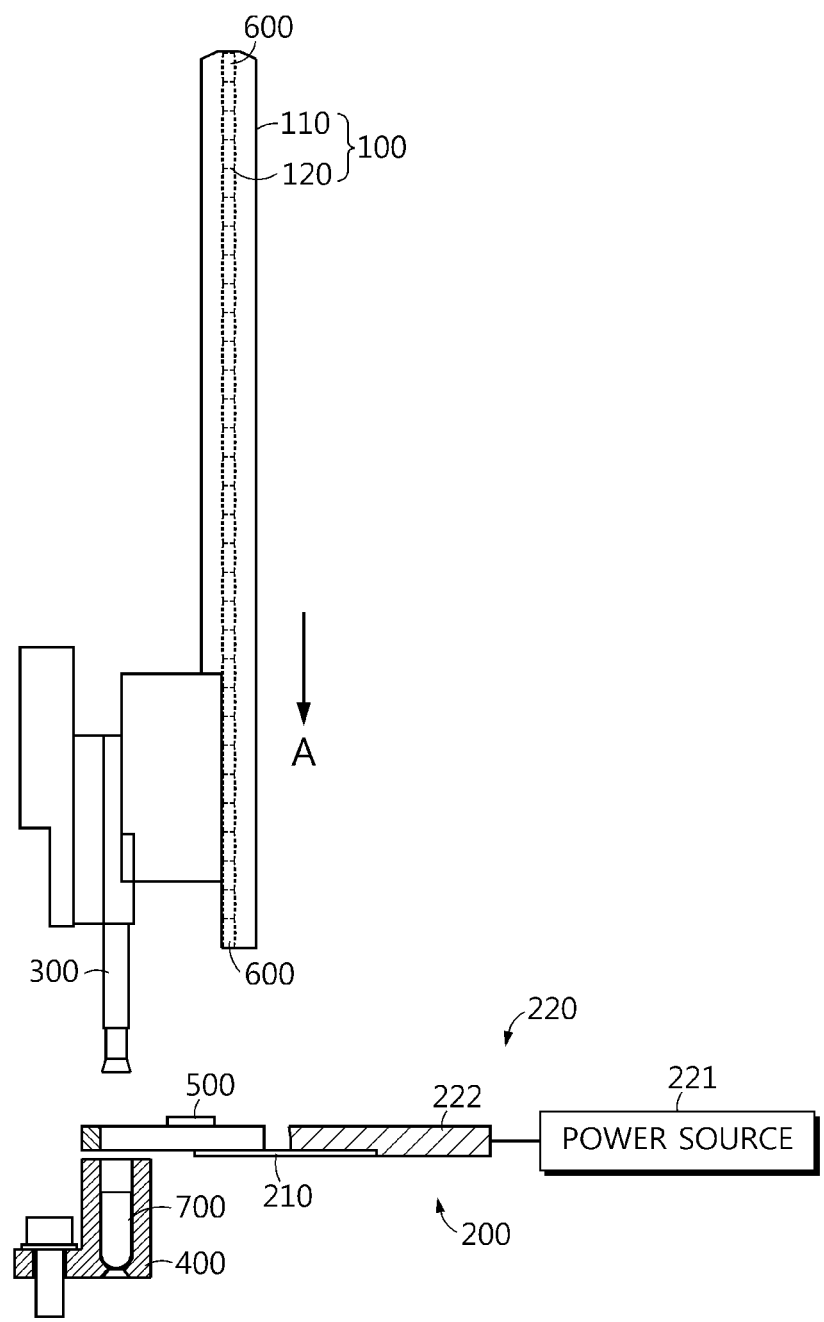
FIGS. 3 to 12 are diagrams for illustrating a process of filling tablets in a capsule using the capsule filling apparatus according to an embodiment of the present disclosure.
Figure 4:
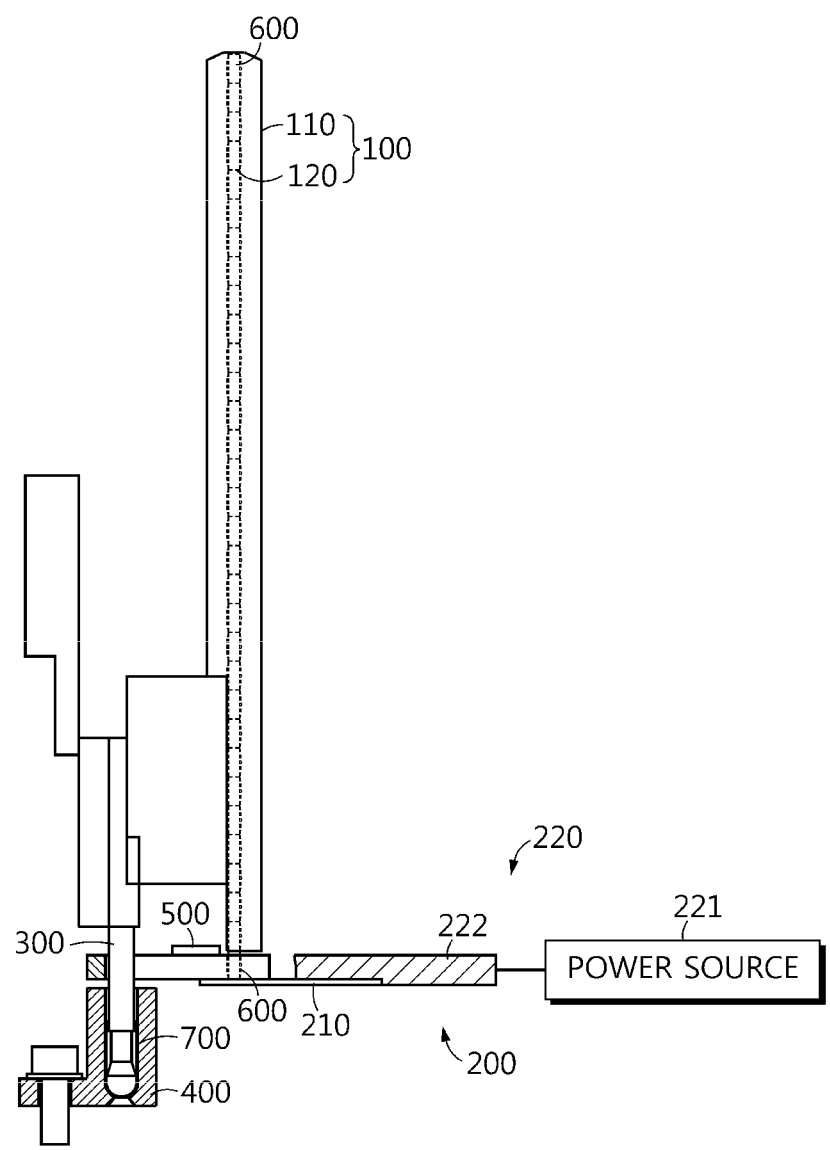
Figure 6:
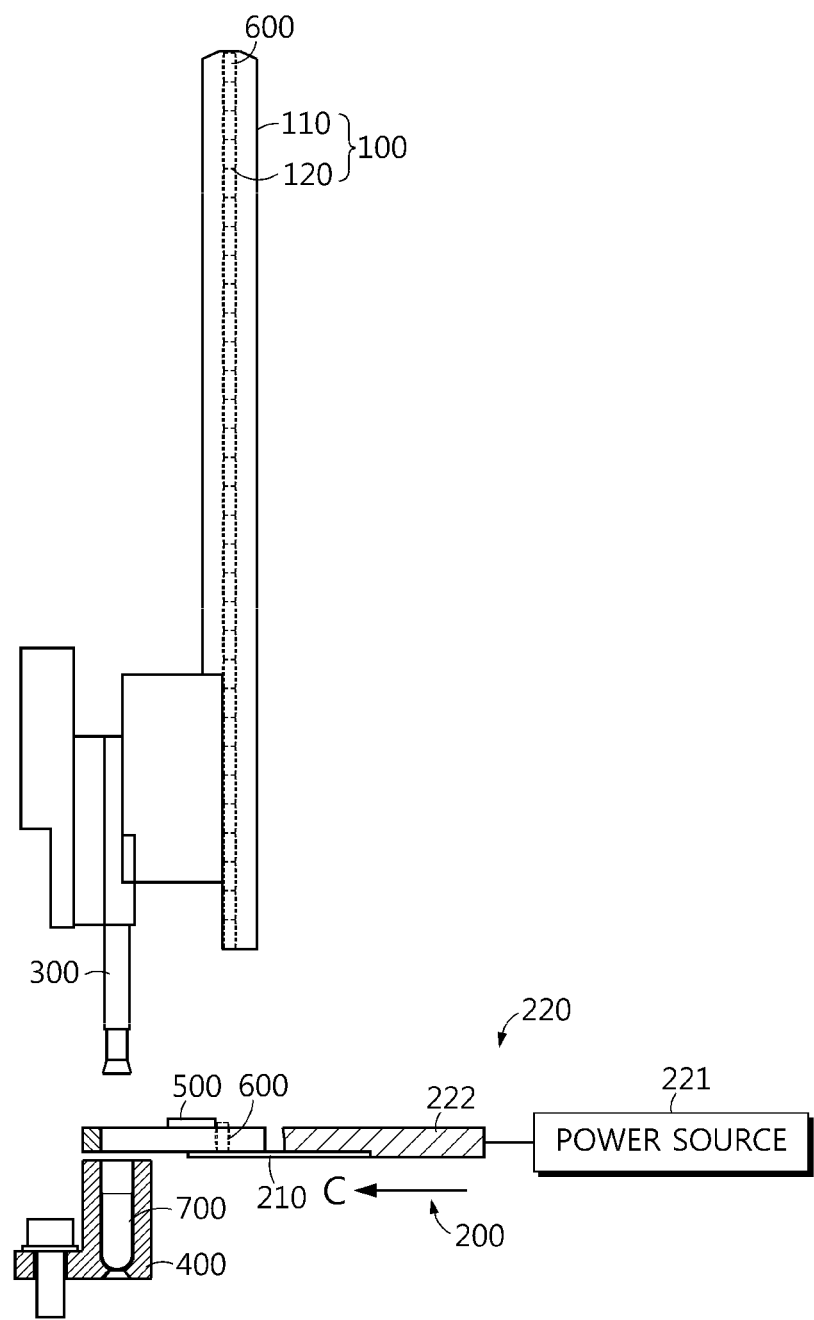
Figure 7:
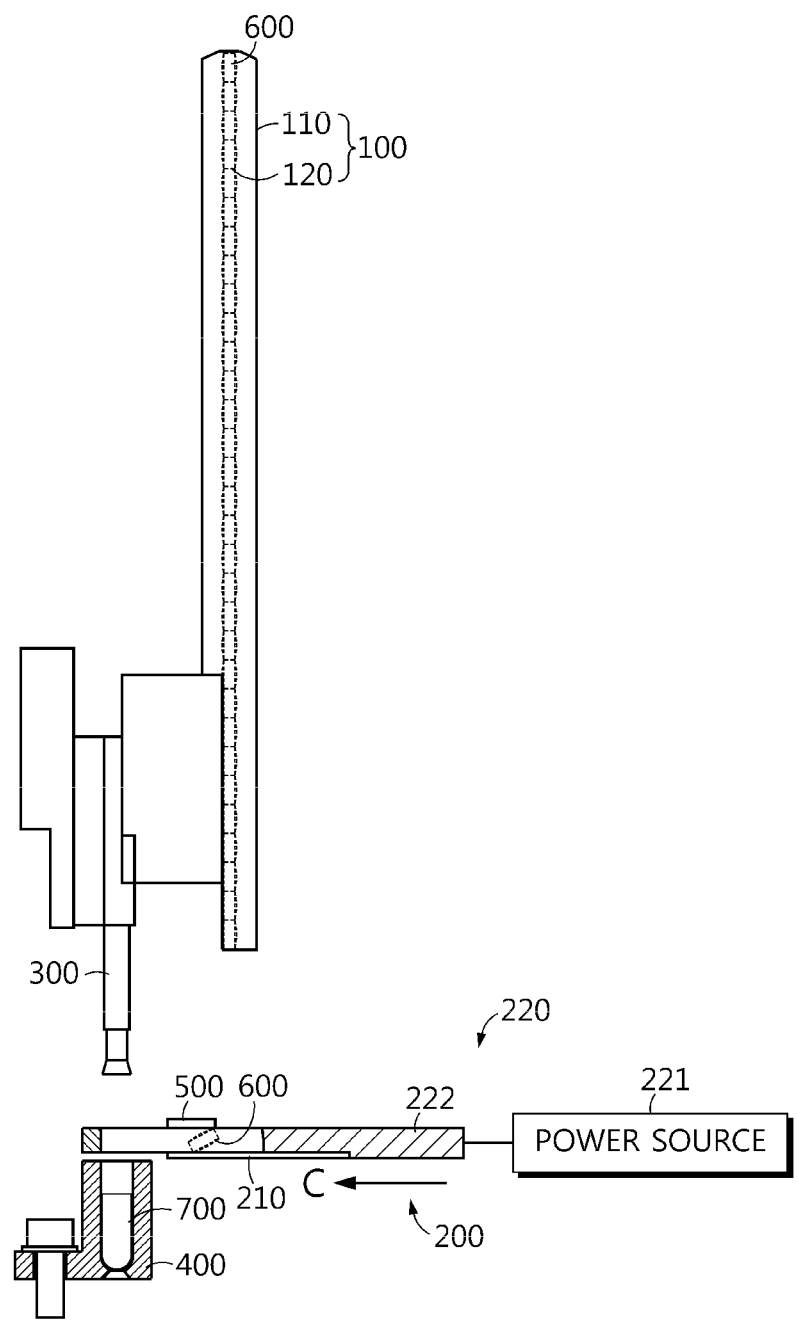
Figure 8:
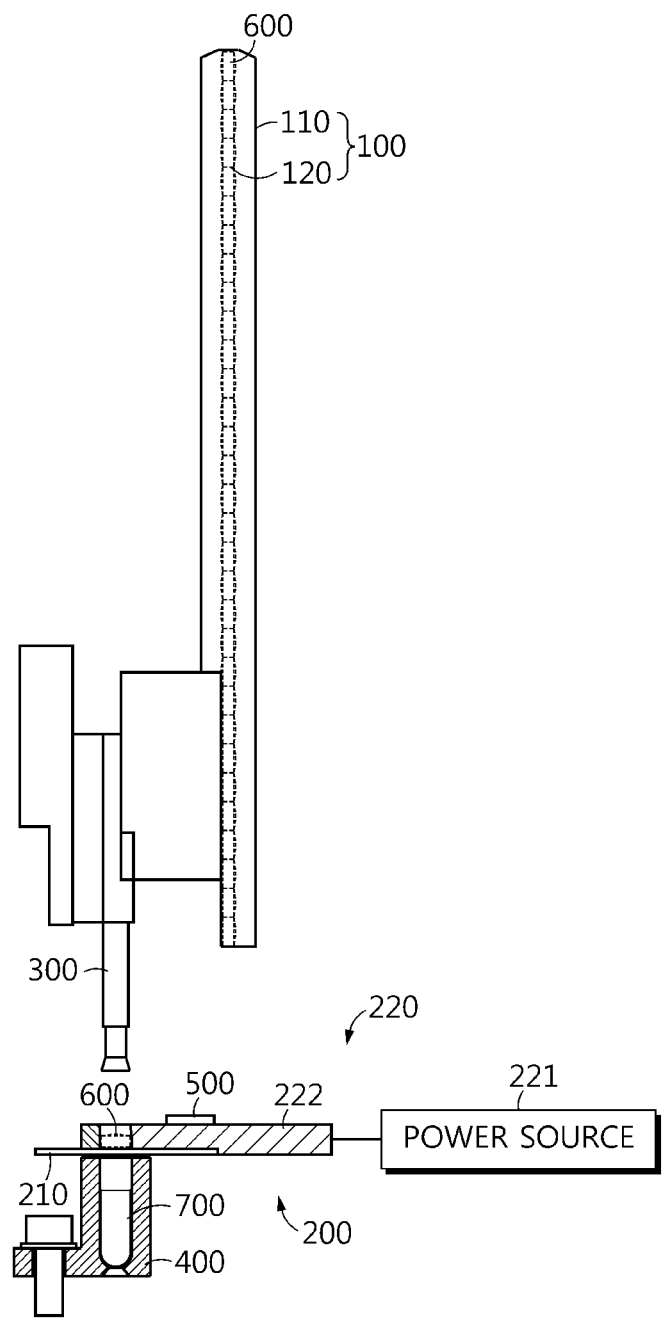
Figure 9:
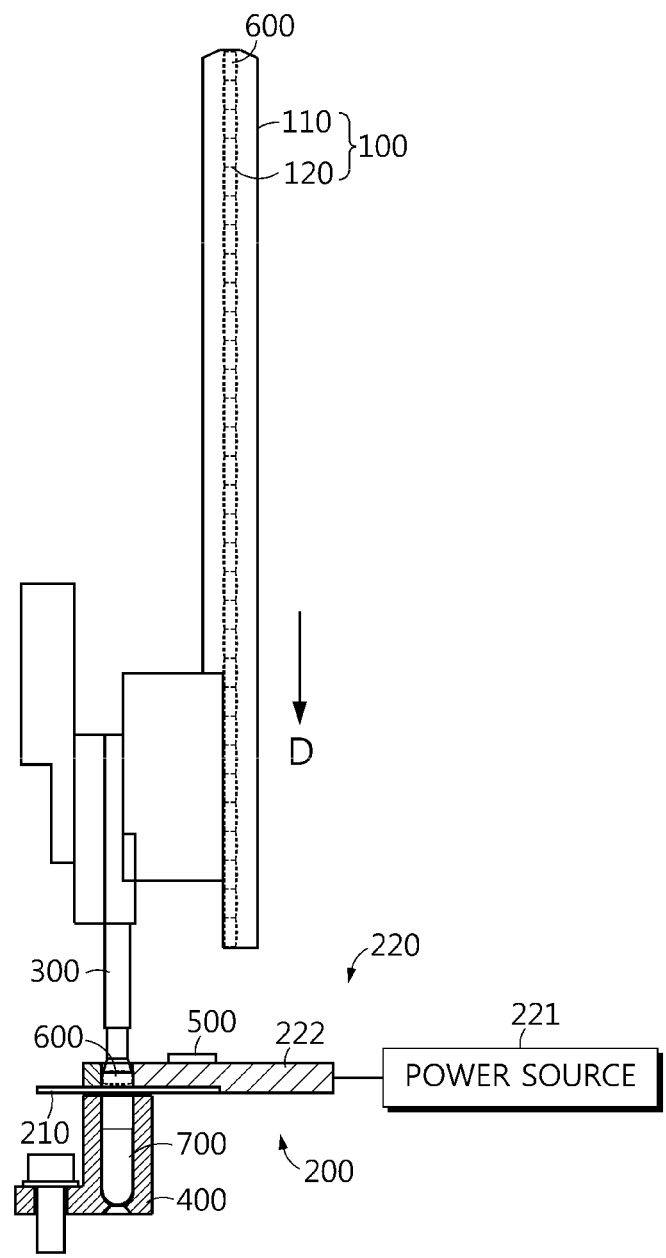
Figure 10:
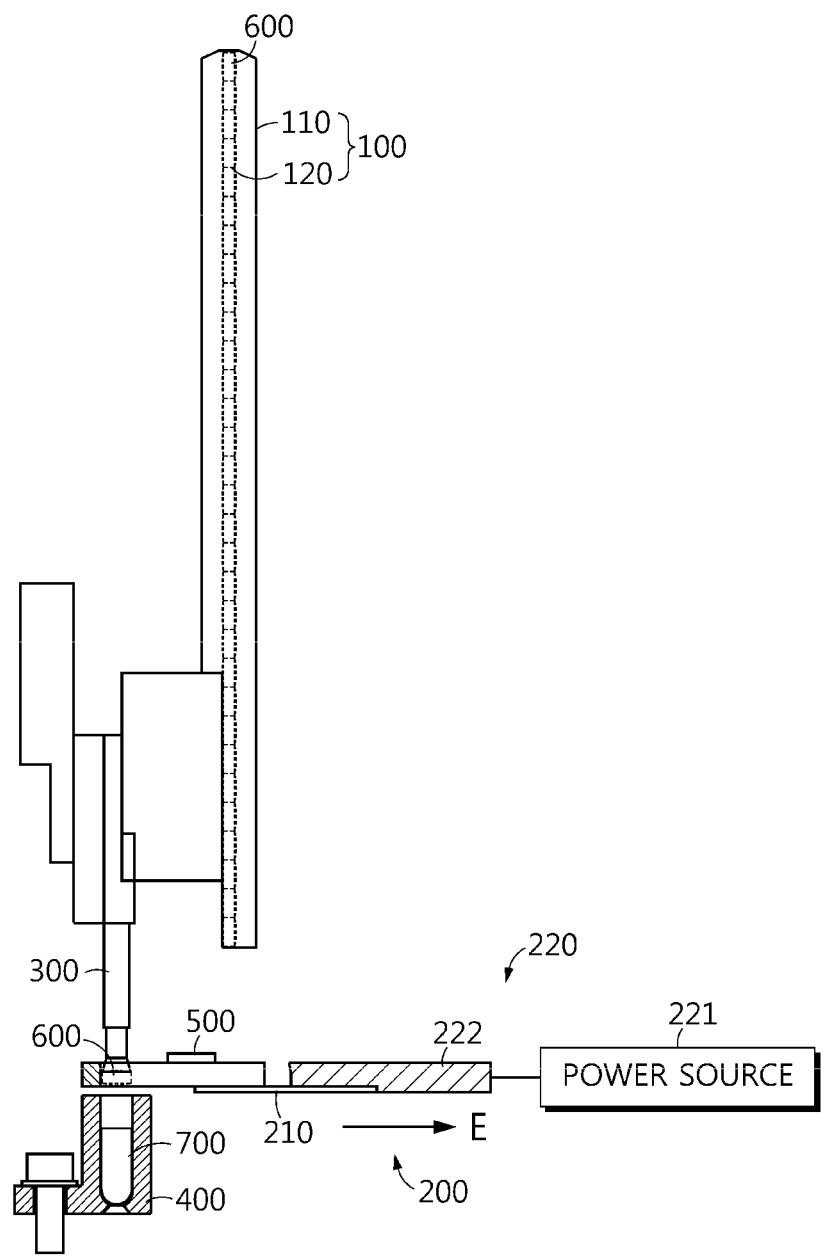
Figure 11:
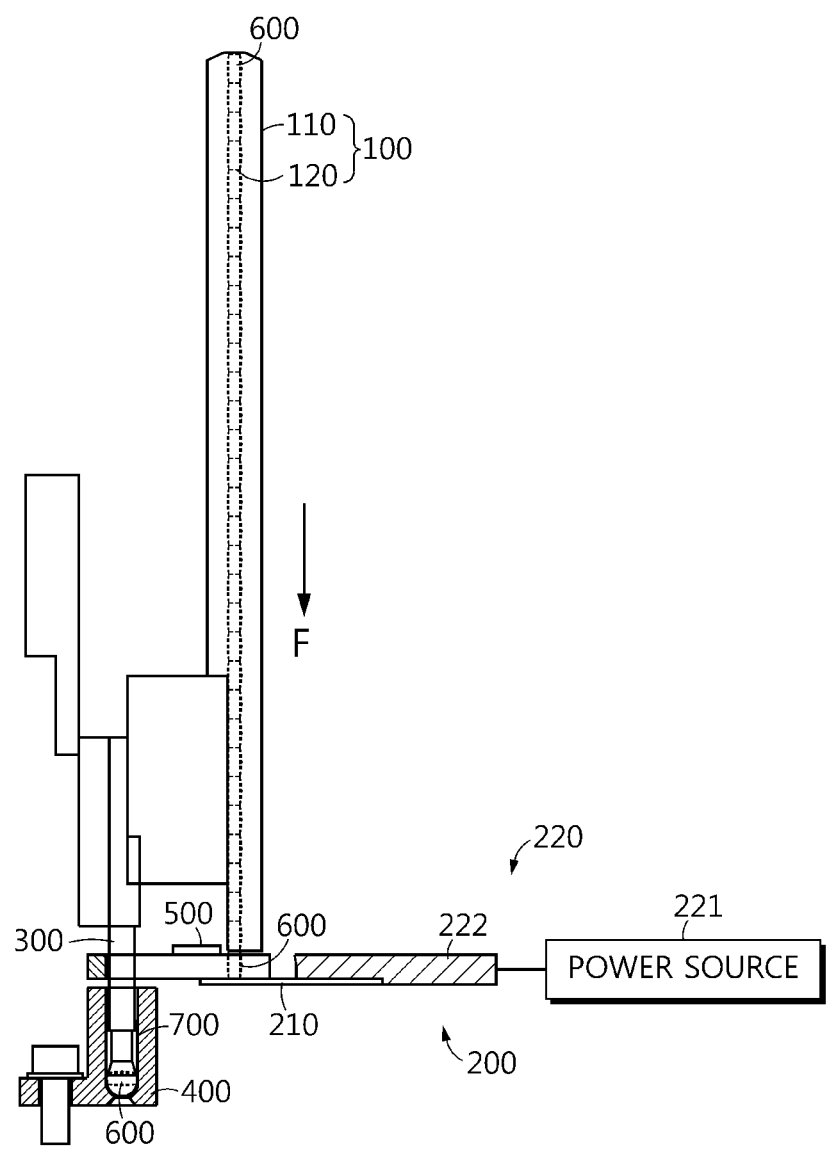
Figure 12:
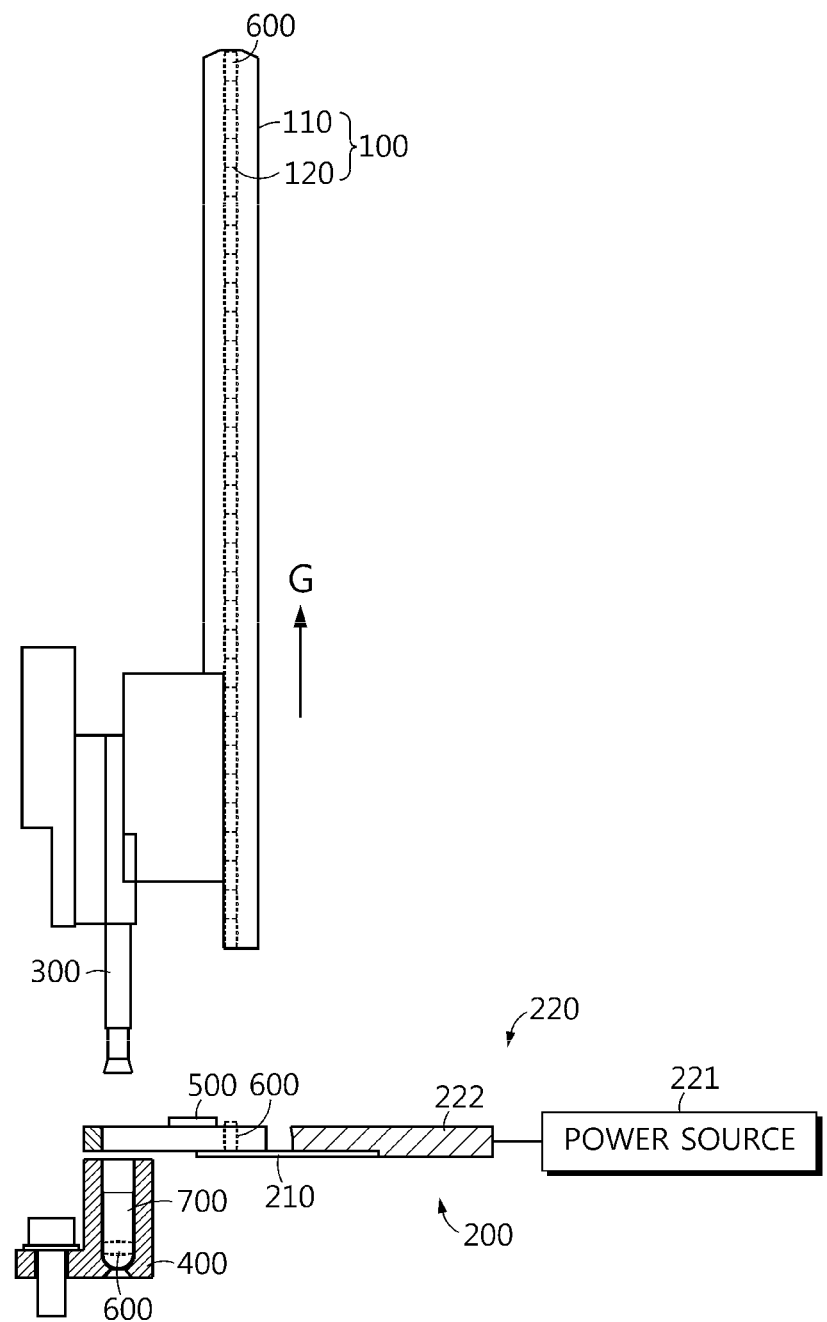

Referring to FIG. 3, the supplying member 100 moves down in an A direction based on FIG. 3 toward the moving member 200. At this time, the catching member 300 coupled to the supplying member 100 also moves down together with the supplying member 100. Referring to FIG. 4, the supplying member 100 moves to the support 210 of the moving member 200, and the catching member 300 is inserted into the capsule accommodating member 400. In addition, if the supplying member 100 moves to the support 210 of the moving member 200, the door (not shown) of the supplying member 100 is opened, and one tablet 600 among the plurality of tablets 600 arranged in the vertical direction at the tablet arranging portion 120 of the supplying member 100 is placed on the support 210. Here, if one tablet 600 is placed on the support 210, the door (not shown) of the supplying member 100 is closed to restrict the discharge of the other tablets 600. Referring to FIG. 5, the supplying member 100 is moved away from the moving member 200, namely in a B direction based on FIG. 5. At this time, the catching member 300 coupled to the supplying member 100 also moves upward together with the supplying member 100. In addition, as shown in FIG. 5, the tablet 600 is placed in the vertical direction on the support 210 of the moving member 200. Referring to FIG. 6, the moving member 200 on which the tablet 600 in the vertical direction is placed moves in a C direction based on FIG. 6 toward the catching member 300 or the capsule accommodating member 400, and the tablet 600 in the vertical direction collides with the aligning member 500 disposed between the catching member 300 and the moving member 200. Referring to FIG. 7, the moving member 200 continues to move in the C direction based on FIG. 7 toward the catching member 300 or the capsule accommodating member 400, and the tablet 600 colliding with the aligning member 500 is inclined. Referring to FIG. 8, the tablet 600 placed on the support 210 of the moving member 200 completely falls down to be arranged in a horizontal direction, and the tablet 600 placed on the support 210 of the moving member 200 is located between the catching member 300 and the capsule accommodating member 400, namely below the catching member 300 and above the capsule accommodating member 400. Referring to FIG. 9, the catching member 300 moves down in a D direction based on FIG. 9 toward the tablet 600 on the support 210. At this time, the supplying member 100 coupled to the catching member 300 also moves down together with the catching member 300. In addition, if the catching member 300 comes into contact with the tablet 600 and catches the tablet 600, as shown in FIG. 10, the moving member 200 moves in an E direction based on FIG. 10, and the tablet 600 is caught by the catching member 300. In addition, referring to FIG. 11, the catching member 300 moves down in an F direction based on FIG. 11 toward the capsule 700 accommodated in the capsule accommodating member 400. In addition, the supplying member 100 coupled to the catching member 300 also moves down together with the catching member 300. In addition, as the adsorption of the catching member 300 is stopped, the tablet 600 correctly aligned in the horizontal direction is filled into the capsule 700. At this time, the supplying member 100 supplies a new tablet 600 in the vertical direction to the support 210 of the moving member 200. By doing so, it is possible to prevent the tablet 600 from being inclined or erected, and also, it is possible to improve the filling rate of the tablets 600 when the tablets 600 are filled in the capsule 700. Referring to FIG. 12, the catching member 300 moves upward in a G direction based on FIG. 12 away from the capsule 700 accommodated in the capsule accommodating member 400. In addition, the supplying member 100 coupled to the catching member 300 also moves upward together with the catching member 300. Here, the capsule 600 accommodated in the capsule accommodating member 400 is filled with the tablet 600 in the horizontal direction, and the tablet 600 in the vertical direction is placed on the support 210 of the moving member 200. In addition, the capsule accommodating member 400 filled with the tablet 600 rotates, so that a new capsule accommodating member 400 is positioned below the catching member 300. Also, the new tablet 600 of FIG. 12 placed in the vertical direction on the support 210 of the moving member 200 is filled in the capsule 700 accommodated in a new capsule accommodating member 400 in the same way as above. The filling process of the capsules 700 may be automated repeatedly performing the above process.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

INDUSTRIAL APPLICABILITY

The present disclosure relates to a capsule filling apparatus and is particularly applicable to industries related to a capsule filling apparatus that may improve the filling rate of tablets.

What is claimed is:
1. A capsule filling apparatus, comprising:
a supplying member configured to supply a tablet;
a moving member configured to move the tablet supplied from the supplying member in a preset direction;
a catching member configured to catch the tablet moved by the moving member by suction and insert the caught tablet into a capsule; and
a capsule accommodating member located below the catching member so that the capsule is accommodated therein,
wherein the catching member inserts the tablet into the capsule by moving into the capsule in a state of catching the tablet, and
wherein when the moving member moves to the capsule accommodating member, the catching member catches by suction the tablet located at the moving member that has moved to the capsule accommodating member, and when the moving member moves away from the capsule accommodating member, the catching member inserts the tablet into the capsule accommodating member from which the moving member has moved away.
2. The capsule filling apparatus according to claim 1, wherein the supplying member is coupled to the catching member to move together with the catching member.
3. The capsule filling apparatus according to claim 2, wherein the supplying member includes:
a cover portion coupled to the catching member; and
a tablet arranging portion formed inside the cover portion so that the tablet is arranged therein.
4. The capsule filling apparatus according to claim 3, wherein the tablet is formed in a cylindrical shape so that a height of a lateral side of the tablet is smaller than a diameter of a base side of the tablet, and
a plurality of tablets are arranged in the tablet arranging portion such that lateral sides of the plurality of tablets are in contact with each other.
5. The capsule filling apparatus according to claim 1, wherein the moving member includes:
a support on which the tablet supplied from the supplying member is placed; and
a driving unit coupled to the support to move the support.

6. The capsule filling apparatus according to claim 5,
wherein the tablet is formed in a cylindrical shape so that a height of a lateral side of the tablet is smaller than a diameter of a base side of the tablet, and the tablet is placed on the support so that the lateral side of the tablet comes into contact with the support.

7. The capsule filling apparatus according to claim 6, further comprising:

an aligning member disposed between the catching member and the moving member such that the tablet collides with the aligning member to fall down while the moving member is moving, so that the base side of the tablet comes into contact with the support.

8. The capsule filling apparatus according to claim 1,
wherein the capsule accommodating member is provided in plural, and the plurality of the capsule accommodating members are provided such that any one capsule accommodating member among the plurality of capsule accommodating members is located below the catching member by rotation.

\* \* \* \* \*